United States Patent [19]

Shimada et al.

[11] Patent Number: 5,042,144

[45] Date of Patent: Aug. 27, 1991

[54] METHOD OF FORMATION OF BIO-ELECTRODE LAMINA

[75] Inventors: Jin Shimada, Falcon Heights; Douglas W. Fletcher, Plymouth, both of Minn.

[73] Assignee: Health Concepts, Inc., Minneapolis, Minn.

[21] Appl. No.: 411,416

[22] Filed: Sep. 22, 1989

[51] Int. Cl.$^5$ .............................. H01R 43/00
[52] U.S. Cl. ........................ 29/825; 29/877; 29/884; 128/641; 128/798; 156/235; 204/418
[58] Field of Search .............. 29/825, 847, 884; 156/235, 244.11; 264/171; 204/418, 415, 419

[56] References Cited

U.S. PATENT DOCUMENTS

| | | | |
|---|---|---|---|
| 3,805,769 | 4/1974 | Sessions | 29/825 |
| 3,998,215 | 12/1976 | Anderson et al. | |
| 4,063,352 | 12/1977 | Bevilacqua | 29/884 |
| 4,274,420 | 6/1981 | Hymes | 128/798 X |
| 4,352,359 | 10/1982 | Larimore et al. | |
| 4,383,079 | 5/1983 | Gasper et al. | |
| 4,409,981 | 10/1983 | Lundberg | 29/825 X |
| 4,461,075 | 7/1984 | Bailey | 29/825 |
| 4,517,326 | 5/1985 | Cordts et al. | |
| 4,563,263 | 7/1986 | Oyama et al. | 204/418 |
| 4,580,339 | 4/1986 | Ioffe | 29/825 |
| 4,617,935 | 10/1986 | Cartmell et al. | |
| 4,635,642 | 1/1987 | Cartmell et al. | 128/641 X |
| 4,795,526 | 1/1989 | Strand | 156/235 |
| 4,798,642 | 1/1989 | Craighead et al. | 29/877 X |
| 4,925,544 | 5/1990 | Goldring | 204/415 X |

OTHER PUBLICATIONS

Anal Chem 1985, 57 1155–1157 by Fogt et al., article titled "Simplified Procedure for Forming Polymer--Based Ion-Selective Electrodes".

*Primary Examiner*—Carl J. Arbes
*Attorney, Agent, or Firm*—Joel D. Skinner; Anthony G. Eggink

[57] ABSTRACT

A method of forming a conductive lamina for use with and to form a bio-medical electrode device comprising the steps of providing a non-conductive base structure, providing a mixture of an electrically conductive substance and a media component, depositing the mixture onto the base structure, and curing the mixture. The method further comprises the step of mixing the electrical conductant and the media component in a closed cell, positive pressure kinetic mixer. The method further comprises the steps of combining a urethane base and a polyhydric alcohol to form the media component and delaying the mixing of the media component and the electrical conductant for a predetermined time period. In another embodiment, the method comprises the steps of combining a photo-initiator, a cross-linking agent, and low pH acrylic monomers to form a precomponent, and mixing the precomponent with the glycol to form the media component. The method further comprises the step of cooling the mixture prior to depositing it onto the base structure, and exposing the mixture to ultraviolet energy for a predetermined time period.

17 Claims, 3 Drawing Sheets

METHOD OF FORMATION OF BIO-ELECTRODE LAMINA

BACKGROUND OF THE INVENTION

This invention relates generally to bio-electrodes and, more particularly, to methods of making conductive and adhesive lamina for use with and to form such electrodes. The methods and electrodes of this invention are particularly useful for transmitting electrical signals between the patient and peripheral medical equipment for diagnostic or therapeutic purposes and for electro-medical grounding applications.

In the past, a variety of electrodes have been utilized to transmit or receive bio-electric signals in medical applications. These electrodes generally comprise a solid electrical conductor such as a plate, an adapter and lead wire for connection to the medical equipment, and a conductive lamina. The lamina typically consists of a gel, or other membrane which contains an ionic material to conduct signals between the electrode plate and the patient. Such lamina are typically prepared separately and, subsequently, applied and combined with other elements to form the complete electrode.

These prior art, pre-formed lamina are typically expensive and inefficient to manufacture and to use with or to form an electrode. They further are limited as to size, shape and thickness, as well as to the choice of conductive compositions utilized. Also, electrodes utilizing pre-formed lamina often distort transmitted signals because of relative movement between the electrode and the body surface. Further, electrical hot spots may be caused by the separation of the conductive lamina from the electrode plate or from an uneven distribution of electrolyte in the lamina. Conversely, the high degree of adhesiveness of some electrodes can cause skin irritations to some patients. Some electrodes, therefore, utilize pastes, creams, gels or liquids to overcome this problem, but this added procedure is time consuming and messy.

Insofar as is known, no electrode has been made or proposed, having lamina formed directly on an electrode base and electrical connection surface, and which will maintain stable physical characteristics and effective signal transmission characteristics for a clinically necessary time period.

SUMMARY OF THE INVENTION

The present invention provides a method of forming a conductive lamina for use with and to form a bio-medical electrode device, comprising the steps of providing a non-conductive base structure, depositing a mixture of an electrically conductive substance and a media component onto the base structure, and curing the mixture, whereby the mixture forms the conductive lamina on the base structure. The method also comprises the addition of an electrical connection to the lamina.

The method further comprises the step of mixing the electrical conductant and the media component in a closed cell, positive pressure kinetic mixer. In one embodiment, the method further comprises the steps of combining a urethane base and a polyhydric alcohol to form the media component and delaying the mixing of the media component and the electrical conductant for a predetermined time period. In another embodiment, the method comprises the steps of combining a photo-initiator, a cross-linking agent, and low pH acrylic monomers to form a precomponent, and mixing the precomponent with the polyhydric alcohol to form the media component. This embodiment further comprises the step of cooling the mixture prior to depositing it onto the base structure. The step of curing the mixture includes exposing it to ultraviolet energy for a predetermined time period.

Another method within the scope of this invention involves the steps of providing an electrical connector to the base structure, and of forming a current dispersion layer on one side of the base structure which is connected to the electrical connector.

The present invention also provides a disposable and self-adhering high frequency bio-medical electrode for placement on the body of a patient and for use with an electro-medical diagnostic or therapeutic apparatus. The electrode comprises a non-conductive base structure layer having first and second sides, a conductive signal transmission layer disposed on the first side of the base structure layer, and means to electrically connect the signal transmission layer to a current source, which means is exposed for contact on the second side of the base structure layer. The electrode further comprises a conductive, adhesive, low impedance lamina layer for providing an adhesive interface between the signal transmission layer and the patient body surface. The lamina layer is disposed on the signal transmission layer and comprises a hydrophilic polymer, a polyhydric alcohol, and an electrolyte which are deposited and cured on the signal transmission layer.

These and other benefits of this invention will become clear from the following description by reference to the drawings.

DESCRIPTION OF THE PREFERRED EMBODIMENT

Figure 1:
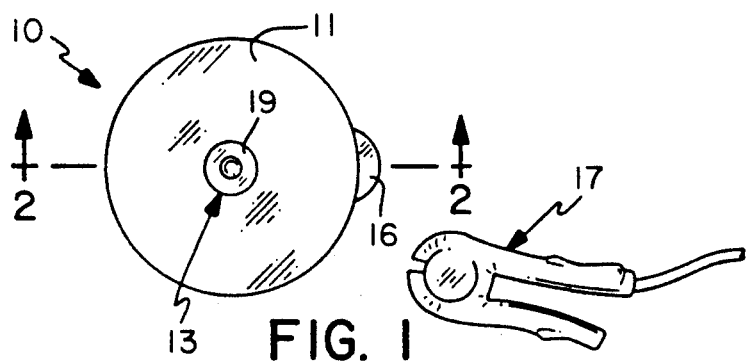
FIG. 1 is a top plan view of the electrode device of the present invention.
Figure 2:
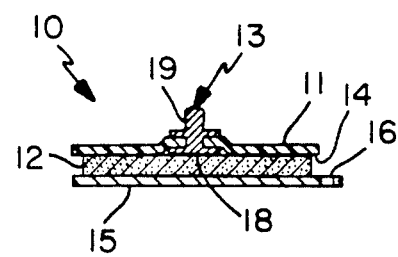
FIG. 2 is a cross-sectional view of the electrode device of FIG. 1, taken along line 2—2.
Figure 3:
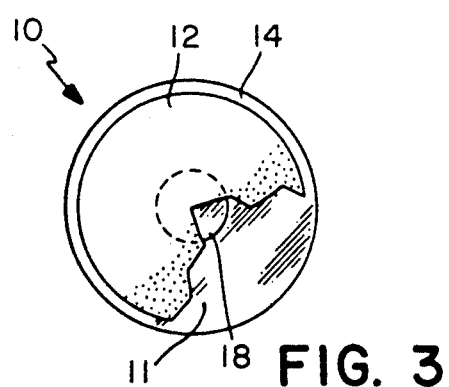
FIG. 3 is a bottom plan view of the electrode device shown in FIG. 1 and having its sanitary release liner removed.

The present invention provides a method of forming a conductive lamina for use with and to form a bio-medical electrode device. The electrode may be used on the body of a patient to transmit or receive bio-electric signals. Referring to FIGS. 1–3, the electrode device 10 has a relatively thin, compact layered structure. In its most basic form, the layered structure includes a base layer 11 and a lamina layer 12. The electrode 10 is shown to have a generally circular shape, but alternative configurations such as an oval, square, or rectangular shape are usable, consistent with the invention.

The base or backing layer 11 provides a structure for containment of the remaining elements of the electrode 10 and for manipulation thereof by the user. It is composed of a thin, flexible and non-conductive substance such as mylar, vinyl, paper, foam tape or the like. The base layer 11, as shown, has a circumferential outer edge portion 14 with respect to the lamina 12. Preferably, both the lamina layer 12 and the patient contact surface of the circumferential edge 14 directly contact the skin when the electrode 10 is applied to the patient. The outer circumferential edge 14 also may have an adhesive applied to its patient contact side to result in that configuration on the patient.

The electrode or lamina layer 12 is a thin, conductive, semi-solid layer which is adhesively disposed on the patient contact side of the base layer 11. This configuration provides a structure for use with or to form electrodes whereby the lamina layer 12 adheres to the electrode structure elements while permitting the removable adherence to the skin of a patient. The low impedance lamina layer 12 conducts a broad range of bio-electric frequencies.

Utilizing the method described below, the horizontal dimension of the lamina 12 is variable depending upon the desired surface area of current application or reception to or from the skin. Additionally, the shape or thickness of the lamina 12 may be varied according to the particular electrode application without detrimental changes in electrode performance.

An adapter or connector structure 13 is shown disposed through the base layer 11. The connector 13 is constructed of a conductive metal and has a plate-like eyelet 18 disposed on the base structure so that it contacts the lamina layer 12. A snap portion 19 is generally disposed on the opposite side of the base layer 11 to communicatively connect with the eyelet 18. The connector 13 electrically connects the electrode 10 with an electro-medical apparatus, such as via the apparatus connector 17, as shown in FIG. 1.

The device 10 preferably has a sanitary release liner or layer 15 affixed to and generally coextensive with the outer edge 14 so that it covers and protects the lamina 12 and outer edge 14. The release liner 15 is placed on the lamina layer 12 subsequent to formation of the lamina 12, and is preferably held in place by the adhesiveness of the lamina 12 itself. Prior to use, the release liner 15 is removed by simply pulling it away from the base layer 11. The release liner 15 is shown to have a tab portion or peel strip 16 which extends slightly beyond the perimeter of the outer edge 14 for ease of grasping by the user.

Figure 4:
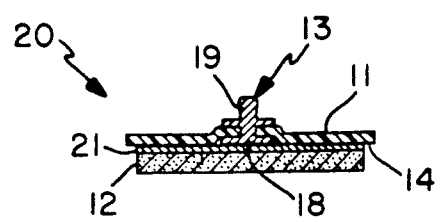
FIG. 4 is a cross-sectional view of another embodiment of the electrode device.

Referring to FIG. 4, another electrode embodiment 20 is shown having a current distribution or dispersion layer 21 which is electrically connected to the adapter 13 and receives electrical current therefrom or distributes current thereto. The current distribution layer 21 is disposed between the base layer 11 and the electrode lamina layer 12. As shown, the current distribution layer 21 consists of a continuous layer of a conductive substance. The conductive substance is preferably a homogeneous, thin layer applied to the base layer 11 by a vapor deposition process. Substances such as carbon film, tin, aluminum, silver/silver chloride ink, carbon ink or the like work particularly well for this purpose. However, additional conductants applied or formed via other means known in the art are usable, consistent with the teachings of this invention. For example, the current distribution layer may comprise a nylon mesh substrate which is coated with a metal, such as silver or copper. The current distribution layer 21 is further shown to be substantially coextensive with the electrode lamina layer 12 to thereby disperse or receive current to or from a greater portion of the surface area of the lamina layer 12. In current transmission applications, this minimizes localized current flow and areas of uneven or differential impedance in the lamina layer 12. In signal reception applications, the current distribution layer 21 improves reception of low level bio-medical signals.

In use, the electrode 10 or 20 is applied to a specific location on the patient body as determined by medical personnel. An apparatus connector 17 (shown in FIG. 1) of a type generally known in the art is then attached to the adapter 13 snap 19 to communicatively connect the electrode 10 or 20 with an electro-medical diagnostic or therapeutic apparatus such as an EKG System. A diagnostic or therapeutic procedure is then performed utilizing the electrode 10 or 20 to receive or transmit bio-electric signals from or to the patient.

Figure 5:
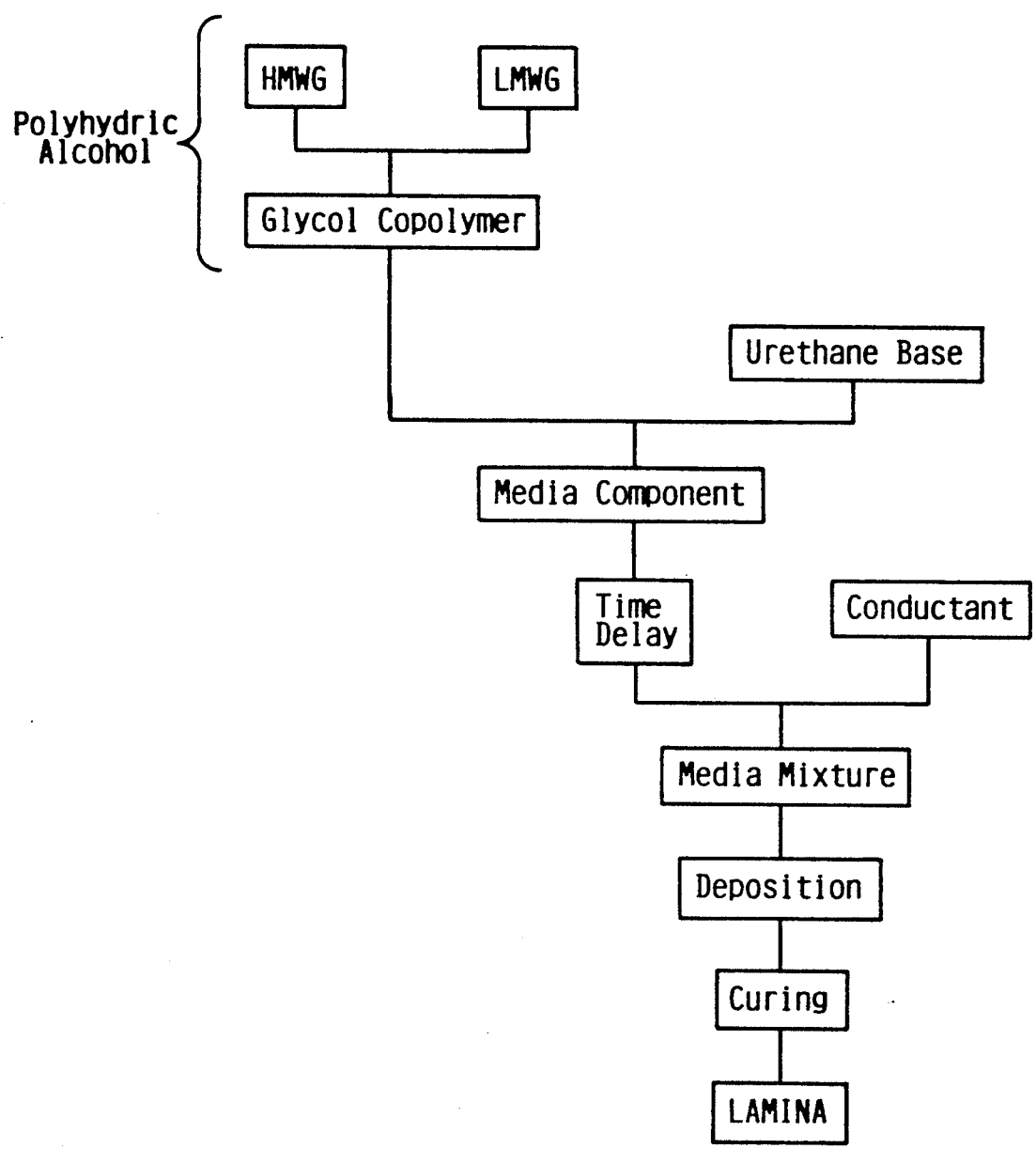
FIG. 5 is a schematic diagram showing the method steps of forming an electrode lamina in accordance with the present invention.

Referring to FIG. 5, the method of forming the electrode lamina of the electrode devices described above is shown in a schematic diagram of method steps and which also shows the chemical components utilized. The preferred means for accomplishing the method is further described below. In its most basic format, the method involves first depositing a viscous, gel-like conductive media mixture directly on an electrode base structure surface and then curing the media mixture in place on the base structure surface. Preferably, the step of curing the deposited media mixture involves allowing the mixture to set for a predetermined time period of 1.5 to 3.5 minutes prior to contacting the lamina or applying any extraneous material such as a release liner. Although the lamina compositions described below are synthetic water soluble resins, water soluble resins derived from known naturally occurring polymers are also usable to practice the teachings of this invention.

One embodiment of the media mixture is a two-part system comprising a mixture of a water soluble polymeric media component and an electrically conductive substance or conductant. Preferably, the media component comprises a hydrophilic urethane base and a polyhydric alcohol which are premixed prior to combination with the conductant. Examples of such urethane base and polyhydric alcohol are polyurethane and an organic glycol, respectively. The mixtures described are combined in a continuous process and preferably the combination of the media component and the conductant is delayed for a predetermined time period subsequent to the formation of the media component. The magnitude of time delay is a function of the total volume of media mixture dispensed per unit time period. It has been found that the preferred order of mixing, as described above, yields preferred minimum curing times.

In another embodiment, the polyhydric alcohol is a copolymer consisting of a mixture of a relatively high molecular weight polyhydric alcohol and a relatively low molecular weight polyhydric alcohol. The composite polyhydric alcohol formed by the mixture of high and low molecular weight polyhydric alcohols may be immediately combined with the hydrophilic urethane base to form the media component. It has been found that an increased ratio of high to low molecular weight polyhydric alcohols yields a relatively firmer or harder consistency to the end product lamina, while a decreased ratio yields a relatively softer or less solid consistency. Such variations in lamina consistency may be utilized to provide higher performance depending upon the specific application of the resultant electrode device formed, for example, where flexibility of the electrode is desired for patient body conforming purposes.

The urethane base is preferably a hydrophilic polyurethane gel, for example, manufactured by Freeman Chemical Corp. or W. R. Grace and Co. Examples of polyhydric alcohols usable in this invention include propylene glycol, polyethylene glycol, glycerine, polypropylene glycol, and ethylene glycol. The conductant is preferably an aqueous electrolyte such as sodium chloride, potassium chloride or potassium citrate. In the preferred embodiment, the media mixture comprises approximately 20 percent by weight urethane base, approximately 50 percent by weight polyhydric alcohol and approximately 30 percent by weight conductant. The resultant media composition consists of macromolecules containing highly purified monomers with a relatively low incidence of unreacted monomers which may cause electrical performance problems.

Figure 6:
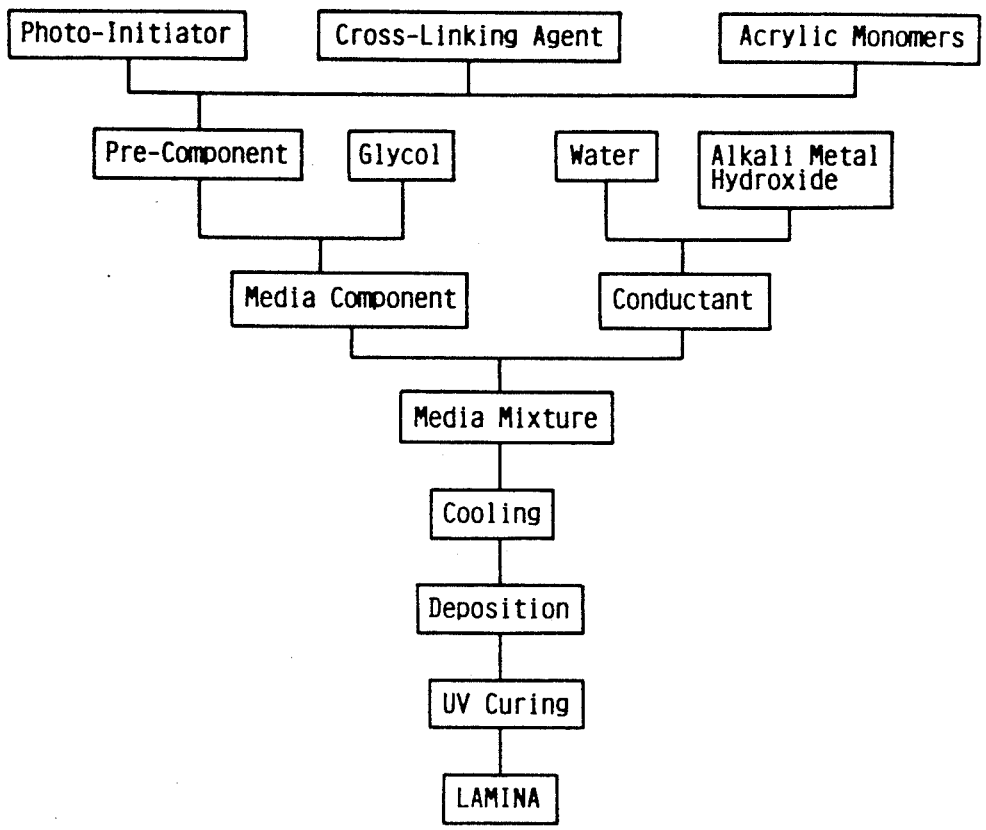
FIG. 6 is a schematic diagram showing the steps of another method in accordance with the invention.

Referring to FIG. 6, another embodiment of the invention is shown in a schematic diagram of method steps and showing the chemical components utilized. This embodiment utilizes the basic method described above with respect to the combination of the media component and conductant. The media component comprises a glycol and a polymeric pre-component which includes a photo-initiator, a cross-linking agent, and acrylic monomers. Glycerol may be substituted for the glycol. Examples of a photo-initiator usable in the pre-component are Irqacure 651 and 184 produced by Ciba-Geigy Corp. Examples of a cross-linking agent include ethyleneglycoldimethylacrylate (EGDM) and diethylglycoldimethylacrylate (DEGDM). The acrylic monomers preferably have a low pH, such as QM-824 acrylic monomers manufactured by Rohm and Haas Co.

The conductant in this embodiment preferably has a high pH, comprising 50 percent by weight water and 50 percent by weight of an alkali metal hydroxide such as sodium hydroxide or potassium hydroxide. Other high pH electrolytes are also usable in this embodiment.

The precomponent, glycol and conductant are shown to be continuously mixed without a time delay. The mixture of these components produces an exothermic reaction and, thus, the method includes the step of a cooling the resultant media mixture prior to deposition. In this embodiment of the method, the deposited media mixture is cured by exposing it to ultraviolet radiation (approximately 250 nm) for approximately 10 seconds.

The lamina formation methods of the present invention are conducted via a closed cell system which prevents the ingress of air so that the moisture sensitive reagents and intermediaries are not contaminated by environmental moisture. Mixing is preferably accomplished in a continuous system and in a non-agitating manner, for example, via a kinetic mixer. The closed cell system is preferably driven by positive pressure means such as a positive pressure gear. The closed cell, positive pressure kinetic mixer system provides completely mixed, homogeneous media compositions which are substantially free of deleterious air or gas bubbles.

Figure 7:
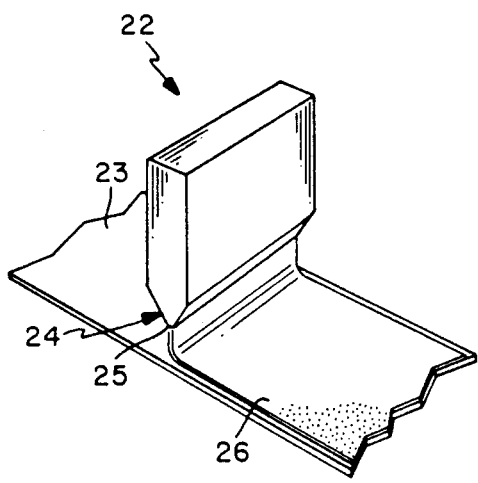
FIG. 7 is a diagram showing a particular method of deposition.
Figure 8:
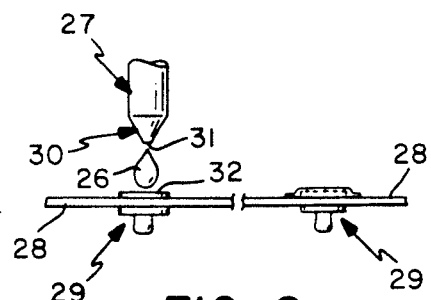
FIG. 8 is a diagram showing another method of deposition.

Referring to FIGS. 7 and 8, the method of depositing the media mixture is accomplished via an egress or deposit means having an aperture of a predetermined configuration, and which is disposed at the terminal end of the closed cell, continuous mixing system. FIG. 7 shows an embodiment of the egress means being an extrusion head 22 which is generally vertically disposed above a length of electrode base structure 23. The extrusion head 22 has a generally rectangular horizontal cross-section with a length which is slightly less than the width of the base structure 23. The extrusion head 22 has a tapered configuration at its bottom end 24 which terminates in a rectilinear extrusion aperture 25 from which the media mixture 26 is dispensed. The dimensions of the extrusion head 22 and aperture 25 are variable to deposit media mixture 26 in various size layers depending upon electrode application. The extrusion aperture 25 is closely disposed a predetermined distance above the base structure 23 so that the media mixture 26 is deposited in a thin, uniform coat or layer on the base structure 23. The thickness of the deposited media mixture is dependent upon the flow rate from the aperture 25 and upon the lateral velocity of the base structure 23 relative to the extrusion head 22.

This system is utilized, for example, in a continuous manufacturing process where the base structure 23 is conveyed at a predetermined velocity under a fixed position extrusion head 22. Subsequent to curing, the base structure 23 is cut or otherwise separated into predetermined sizes or lengths to form, for example, individual planar or roll-type units of material. Additionally, a sanitary release liner (not shown) may be applied to the cured lamina layer. Electrical connectors are subsequently provided to the lamina layer as discussed previously with respect to FIG. 1.

FIG. 8 shows another egress means embodiment which is a dispensing head 27 that is generally vertically disposed above a conveyance mechanism which propels a stream of individual base structures 28 of a predetermined dimension, each shown to have a snap and eyelet-type electrical connector 29. Alternatively, the electrical connectors 29 may be disposed at predetermined intervals on a continuous length of base structure sheeting (not shown), which is perforated at selected intervals for later separation by the user, or which may be cut later in the electrode manufacturing process. The dispensing head 27 is shown to have a generally cylindrical configuration, tapered at its bottom end 30, and which has a terminal circular aperture 31. The media mixture 26 is emitted from the aperture 31 in predetermined quantities, for example, approximately 0.5 grams depending upon layer thickness and size. The dispensed media mixture 26 is deposited at the site of the electrical connector 29 on its patient contact side where it is shown to fully coat the eyelet 32, via flow, to form a generally circular layer. Thereafter, the media mixture is cured.

In summary, the conductive adhesive lamina provides an improved interface between the electrical transmitter and the patient's skin thereby minimizing noise or distortion typically associated with electrode contact interfaces. The lamina contains a relatively high proportion of liquid to provide improved adherence to and comfort on the skin. However, the lamina also remains easy to remove from the patient's skin without irritation and with minimum residue. Such residues of prior art electrode lamina are messy and may cause irritation if left on the patient. Furthermore, the high concentration of liquid contained in the conductive lamina provides high quality electrical conductance for improved signal transmission, extended life for medical apparatus battery systems, and reduced variable impedance.

The lamina is formed directly on the electrode, and thus, will not evaporate as in conventional electrode gels or pastes, nor will it easily leak, drip or run, as do these prior art substances. Importantly, direct formation of the lamina on the base structure layer also allows greater manufacturing flexibility as well as economy. The methods of this invention are applicable to the manufacturing of electrodes used in a variety of different diagnostic and therapeutic applications such as electro-cardiography and cardiac defibrillation.

As many changes are possible to the embodiments of this invention utilizing the teachings thereof, the descriptions above and the accompanying drawings should be interpreted in the illustrative and not in the limited sense.

That which is claimed is:

1. A method of forming a conductive lamina for a bio-medical electrode structure, comprising the steps of:
   a. providing a non-conductive base structure;
   b. combining a urethane base and a polyhydric alcohol to form a media component;
   c. mixing an electrically conductive substance with said media component;
   d. depositing said mixture onto said base structure; and
   e. curing said mixture on said base structure, whereby said mixture forms a conductive lamina on said base structure.

2. The method of claim 1, wherein said base structure consists of a thin layer of material having first and second opposing sides, and further comprising the step of providing means to electrically connect said first and second sides of said base structure.

3. The method of claim 2, wherein said step of providing means to electrically connect includes the steps of placing a conductive eyelet on said first side of said base layer, placing a conductive snap on said second side of said base structure, and connecting said snap to said eyelet through said base structure.

4. The method of claim 2, further comprising the step of providing a current dispersion layer on said first side of said base structure, to thereby electrically connect said dispersion layer with said means to electrically connect.

5. The method of claim 4, wherein said step of providing said current dispersion layer includes applying a conductive substance to said base layer by vapor deposition, said substance being selected from the group consisting of carbon film, tin, aluminum, silver/silver chloride ink, and carbon ink.

6. The method of claim 4, wherein said step of providing said current dispersion layer includes applying a nylon mesh substrate coated with a metal to said base layer.

7. The method of claim 1, further comprising the step of delaying the mixing of said media component and said electrical conductant for a predetermined time period subsequent to said step of combining said urethane base and said polyhydric alcohol.

8. The method of claim 1, wherein said polyhydric alcohol is a glycol copolymer, and further comprising the step of combining a high molecular weight glycol and a low molecular weight glycol to form said glycol copolymer.

9. The method of claim 1, further comprising the steps of combining a photo-initiator, a cross-linking agent, and low pH acrylic monomers to form a precomponent, and mixing said precomponent with a glycol to form said media component.

10. The method of claim 9, further comprising the step of cooling said mixture prior to said step of depositing said mixture onto said base structure, and wherein said step of curing said mixture includes exposing said mixture to ultraviolet energy for a predetermined time period.

11. The method of claim 1, wherein said step of depositing said mixture includes extruding a continuous stream of said mixture on said base structure.

12. The method of claim 11, wherein said base structure is a sheet of material having a predetermined width and a predetermined length, and further comprising the step of propelling said base structure sheet in a lengthwise direction, whereby a said mixture is deposited on said base structure sheet in a continuous layer.

13. The method of claim 12, further comprising the step of separating said base layer sheet at predetermined intervals to provide individual electrodes.

14. The method of claim 2, wherein said step of depositing said mixture includes dispensing a predetermined amount of said mixture onto said base structure in contact with said means to electrically connect and permitting said mixture to flow into a generally circular configuration thereon.

15. The method of claim 2, comprising the step of providing said means to electrically connect at a plurality of predetermined locations on said base structure, said base structure having a predetermined length, and further comprising the steps of moving said base structure in a lengthwise direction, dispensing said mixture at each said means to electrically connect so that said mixture is deposited on said means to electrically connect, and separating said base structure at predetermined locations between said means to electrically connect to form individual electrodes.

16. A method of making a disposable, self-adhering lamina for use with a bio-medical electrode structure for placement on the body surface of a patient and adapted to be used with an electro-medical diagnostic or therapeutic apparatus, comprising the steps of:
   a. providing a non-conductive base structure layer;
   b. mixing a hydrophilic media component comprising a urethane base and a polyhydric alcohol, and a conductant without agitation in a closed cell, positive pressure system to form a mixture;
   c. depositing said mixture from said closed cell system onto said base structure layer; and
   d. curing said mixture for a predetermined time period, whereby said mixture forms a semi-solid, conductive and adhesive lamina on said base structure.

17. A method of making a disposable, self-adhering bio-medical electrode for placement on the body surface of a patient and for use with an electro-medical diagnostic or therapeutic apparatus, comprising the steps of:
   a. providing a non-conductive base structure layer having first and second sides;
   b. forming a conductive signal transmission layer on said first side of said base structure layer;
   c. providing means to electrically connect said signal transmission layer to the electro-medical apparatus, said means to connect being exposed for contact on said second side of said base structure layer;
   d. mixing a hydrophilic, urethane base with a polyhydric alcohol in a closed cell, positive pressure kinetic mixer system to form a water soluble resin;

e. mixing said resin with a conductant to form a hydrophilic media mixture;
f. depositing said media mixture from said closed cell system on said signal transmission layer; and
g. curing said media mixture for a predetermined time period, whereby said media mixture forms a conductive, adhesive, low impedance, semi-solid lamina layer on said signal transmission layer.

* * * * *